United States Patent [19]

Schonenberger et al.

[11] Patent Number: 4,598,091
[45] Date of Patent: Jul. 1, 1986

[54] (1,2-DIPHENYL)-ETHYLENEDIAMINE)-PLATINUM (II) COMPLEX COMPOUNDS

[75] Inventors: Helmut Schonenberger, Pentling; Beate Wappes, Regensburg; Margaretha Jennerwein, Regensburg; Erwin von Angerer, Regensburg; Jurgen Engel, Alzenau, all of Fed. Rep. of Germany

[73] Assignee: Degussa Aktiengesellschaft, Frankfurt, Fed. Rep. of Germany

[21] Appl. No.: 580,238

[22] Filed: Feb. 15, 1984

[30] Foreign Application Priority Data

Feb. 18, 1983 [DE] Fed. Rep. of Germany ....... 3305636

[51] Int. Cl.⁴ ............... A01N 55/02; A61K 31/32; C07F 15/00
[52] U.S. Cl. ..................................... 514/492; 556/137
[58] Field of Search ................ 260/429 R; 556/137; 514/492

[56] References Cited

U.S. PATENT DOCUMENTS

| | | | |
|---|---|---|---|
| 4,250,189 | 1/1981 | Hydes et al. | 260/429 R X |
| 4,271,085 | 6/1981 | Amundsen et al. | 260/429 R |
| 4,339,437 | 7/1982 | Rosenberg . | |
| 4,410,544 | 10/1983 | Berg et al. . | |
| 4,431,666 | 2/1984 | Bulten et al. . | |
| 4,477,387 | 10/1984 | Kidani et al. | 260/429 R |
| 4,482,569 | 11/1984 | Bulten et al. . | |

FOREIGN PATENT DOCUMENTS

| | | | |
|---|---|---|---|
| 2927056 | 1/1980 | Fed. Rep. of Germany . | |
| 2473946 | 7/1981 | France . | |
| 56-103192 | 8/1981 | Japan . | |
| 57-156416 | 9/1982 | Japan | 260/429 R |
| 2019399 | 10/1979 | United Kingdom | 260/429 R |
| 2055377 | 3/1981 | United Kingdom . | |

OTHER PUBLICATIONS von Angerer, J. Medicinal Chemistry, vol. 25, pp. 832-837 (1982).
Vögtle et al, Chemische Berichte, vol. 109, pp. 1-40 (1976).
Chem. Abst., vol. 96, 193435j (1982).
Berichte (1884) pp. 2404-2405.
Z. Anorganische und allegememi Chemie, vol. 242, p. 113 (1939).
Rec. trav. chim. P. B., vol. 59, pp. 407-422 (1940).
J. Chem. Soc. (1935) pp. 839-846.
Inorg. Chem., vol. 21, pp. 2006-2014, May, 1982.
Chem. Abst., vol. 97, 33374f (1982).
Che. Abst., vol. 95, 73415k (1981).
J. Clin. Hematol. Oncol., vol. 11, No. 2, pp. 47-53.
J. Med. Chem., vol. 25, pp. 952-956 (1982).
J. Med. Chem., vol. 24, pp. 508-515 (1981).

*Primary Examiner*—Helen M. S. Sneed
*Attorney, Agent, or Firm*—Cushman, Darby & Cushman

[57] ABSTRACT

There are prepared antitumor active (1,2-diphenyl-ethylenediamine)-platinum (II) complex compounds of the formula

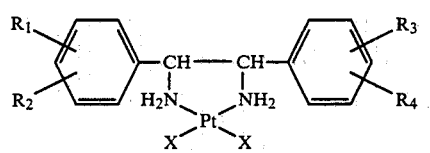

where the groups $R_1$, $R_2$, $R_3$ and $R_4$ are the same or different and are hydrogen, hydroxy groups, $C_1$-$C_6$-alkoxy groups, $C_2$-$C_6$-alkanoyloxy groups which optionally are substituted by halogen atoms or $C_1$-$C_4$-alkanesulfonyloxy groups or $C_3$-$C_6$-alkenoyloxy groups and at least one of $R_1$, $R_2$, $R_3$ and $R_4$ is not hydrogen and X is the equivalent of a physiologically compatible or pharmaceutically acceptable anion.

14 Claims, No Drawings

(1,2-DIPHENYL)-ETHYLENEDIAMINE)-PLATINUM (II) COMPLEX COMPOUNDS

BACKGROUND OF THE INVENTION

There are described in Japanese publication 81-103192 (Chem. Abstract, Selects-Antitumor Agents, Issue 13, (1982), page 10, 96:193435j) stilbenediamine platinum-complexes of the following formula

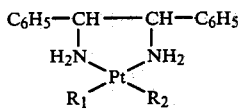

In the formula the group $R_1$ and $R_2$ are halogen, $NO_3$, $SO_4$, OH, or glucuronic acid groups. An antitumor activity is stated for these compounds.

SUMMARY OF THE INVENTION

The invention is directed to (1,2-diphenyl-ethylenediamine)-platinum-(II)-complex compounds of the formula

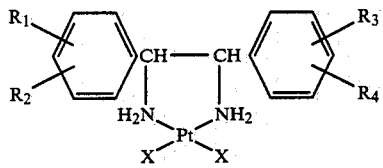

where the groups $R_1$, $R_2$, $R_3$, and $R_4$ are the same or different and are hydrogen, hydroxy groups, $C_1$–$C_6$-alkoxy groups, $C_2$–$C_6$-alkanoyloxy groups which optionally are substituted by halogen atoms or $C_1$–$C_4$-alkanesulfonyloxy groups or $C_3$–$C_6$-alkenoyloxy groups and at least one of $R_1$, $R_2$, $R_3$, and $R_4$ is not hydrogen and X is the equivalent of a physiologically compatible or pharmaceutically acceptable anion.

The invention also includes the preparation of compounds of formula I by reacting a tetrahalogeno-platinum (II)-acid or an alkali-tetrahalogeno-platinum (II)-complex salt with a compound of the formula

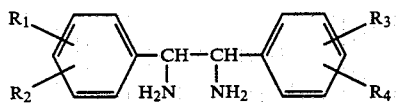

where $R_1$, $R_2$, $R_3$, and $R_4$ are as defined above and at least one of the groups $R_1$, $R_2$, $R_3$, and $R_4$ is not hydrogen or an acid addition salt of a compound of formula II, in a given case there is introduced in free phenolic hydroxyl groups present $C_2$–$C_6$-alkanoyl groups or such alkanoyl groups in a given case substituted by halogen atoms or $C_1$–$C_4$-alkanesulfonyloxy groups, or $C_3$–$C_6$-alkenoyl groups and in a given case, in a compound of formula I the X group or the X group is exchanged to a different physiologically compatible anion.

The invention also includes medicines containing a compound of formula I together with conventional carriers and/or diluents or adjuvants.

The invention further includes the production of a medicine by working a compound of formula I with customary pharmaceutical carriers or diluents or other adjuvants to a pharmaceutical preparation or bringing it into a therapeutically useful form.

The new compounds of the invention possess a decided tumor retarding action together with good compatibility. The tumor retarding action is shown especially with the following animal and cell culture models: Leukemia (for example, Leukemia L5222 of the rat), plasma cell tumors (for example, plasmacytoma ADJ/PC6 of the mouse), hormone dependent tumors (DMBA induced and NMU induced mammary carcinoma of the rat, human MCF 7-mammary carcanoma).

Furthermore, they also have a cytostatic action on hormone independent mammary carcinoma cells (MDA MB 231).

In comparison to the known compounds of Japanese published application 81-103192 the compounds of the invention for example, have a stronger tumor retarding effect at lower toxicity.

In comparison to the known antitumor acting material cisplatin (cis-dichloro-diamine-platinum (II)) the compounds of the invention have a lower toxicity, especially a lower renal toxicity. This follows from investigations of the blood picture, the blood urea concentration and the kidney histology of correspondingly treated animals (mice). The same is true for example, also in regard to damages to the intestinal epithelium. Likewise, the compounds of the invention have an extraordinarily slight bone marrow toxicity.

The following data is directed to preferred illustrative forms of the invention. The $C_1$–$C_6$-alkoxy groups and the $C_2$–$C_6$-alkanoyloxy groups, in a given case, substituted as stated, can be straight or branched and consist of in the case of alkoxy groups, preferably 1 to 4 carbon atoms, in the case of $C_2$–$C_6$-alkanoyloxy groups of 2 to 4 carbon atoms. The $C_3$–$C_6$-alkenoyloxy groups likewise can be straight or branched and especially consist of 3 or 4 carbon atoms. As halogen substituents there can especially be used bromine, chlorine and/or fluorine. The alkanoyloxy grouups can contain one or more (for example, 1 to 6, especially 1 to 3) of the same or different halogen atoms. Particularly there are located 1, 2, or 3, halogen atoms on one carbon atom, preferably on the α-carbon atom. Furthermore, the halogen atoms as well as the alkanesulfonyloxy group may be located preferably in the β-position of the alkanoyloxy group. For example, there is present the methane or ethanesulfonyloxy group. Also there can be present the butanesulfonyloxy group.

Examples of compounds of formula I $R_1$ is as defined above (especially OH) and is in the 2, 3, or 4 position of the phenyl ring while $R_2$, $R_3$, and $R_4$ are hydrogen, $R_1$ and $R_3$ are as defined above (especially OH) and are in the 2, 3, or 4 position, while $R_2$ and $R_4$ are hydrogen, $R_1$ and $R_2$ as well as $R_3$ and $R_4$ are as defined above (especially OH) and are located preferably in case in the 3 and 4 position of the two phenyl rings; $R_1$ and $R_2$ are located preferably in the 3 and 4 positions while $R_3$ and $R_4$ are hydrogen. Examples of the individual definitions of the groups $R_1$, $R_2$, $R_3$, and $R_4$ are hydroxy, methoxy, ethoxy, propoxy, butoxy, hexoxy, acetoxy, propionyloxy, butyryloxy, valeroyloxy, bromoacetoxy, chloroacetoxy, fluoroacetoxy, β-bromopropionyloxy, β-chloropropionyloxy, β-fluoropropionyloxy, α-chloropropionyloxy, dichloroacetoxy, difluoroacetoxy, trichloroacetoxy, trifluoroacetoxy, acryloyloxy, methacryloyloxy, crotonyloxy.

Especially there are included compounds within formula I where both phenyl rings contain the same substituents in the same positions or those compounds where only the one phenyl ring contains one or two of the stated substituents. Compounds with especially favorable properties for example, are those wherein both phenyl rings contain in the 4-position or in the 3-position in each case a hydroxyl group (1,2-bis-(4-hydroxyphenyl)ethylenediamine or 1,2-bis-(3-hydroxyphenyl)ethylenediamine derivatives), namely both in the form of the racemate and also the enantiomers.

The group X represents the known and customary physiologically compatible and pharmaceutically usable (pharmaceutically acceptable) anions of mono or polybasic acids. Especially there can be used, for example, the anions of the following acids: HBr, HCl, HI, $HNO_3$, $H_2SO_4$, $(SO_4^{--})$, $H_3PO_4$ $(HPO_4^{--})$; camphor sulfonic acid, aliphatic or aromatic sulfonic acids, for example $C_1$–$C_6$-alkanesulfonic acids (for example, methanesulfonic acid, ethanesulfonic acid, propanesulfonic acid, butanesulfonic acid, or hexanesulfonic acid), benzene or naphthalenesulfonic acids which in a given case, are substituted once or twice by methyl groups (toluenesulfonic acid, especially o-toluenesulfonic acid, p-toluenesulfonic acid); aliphatic $C_2$–$C_4$-monocarboxylic acids which in a given case, are substituted once, twice or three times by halogen atoms (especially Cl,F) (for example, acetic acid, propionic acid, chloroacetic acid, dichloroacetic acid, trifluoroacetic acid, trichloroacetic acid); aliphatic $C_2$–$C_{11}$ dicarboxylic acids, which in a given case, contains a double bond (for example, oxalic acid, malonic acid, malonic acid which is substituted in the 2-position by one or two $C_1$–$C_4$-alkyl groups, (e.g. methylmalonic acid, butylmalonic acid), maleic acid, fumaric acid, succinic acid, glutaric acid, suberic acid), aliphatic monohydroxy and dihydroxymono-carboxylic acid with 2 to 6, especially 2 to 3 carbon atoms whereby they are preferably α-monohydroxycarboxylic acids such as lactic acid, glyceric acid or glycolic acid, aliphatic monohydroxy and dihydroxy di and tricarboxylic acids having 3 to 8 carbon atoms, especially 3 to 6 carbon atoms such as tartronic acid, malic acid, tartaric acid, malonic acid which is substituted on the middle carbon atom by a hydroxy group and in a given case, a $C_1$–$C_4$-alkyl group, isocitric acid or citric acid; phthalic acid, which in a given case, is substituted by a carboxyl group (especially in the 4-position), isophthalic acid, terephthalic acid, gluconic acid, glucuronic acid, 1,1-cyclobutanedicarboxylic acid, organophosphoric acids such as aldose and ketose phosphoric acids (for example, the corresponding mono- and diphosphoric acids), for example aldose-6-phosphoric acids such as D- or L-glucose-6-phosphoric acid, α-D-glucose-1-phosphoric acid, D-fructose-6-phosphoric acid, D-galactose-6-phosphoric acid, D-ribose-5-phosphoric acid, D-fructose-1,6-diphosphoric acid, glycerine phosphoric acids (whereby the phosphoric acid residue is bound to the end or middle glycerine oxygen atom) such as α-D,L-glycerine phosphoric acid, β-glycerine phosphoric acid, N-phosphonoacetyl-aspartic acid (for example L-aspartic acid).

Formula I also includes the enantiomers and diastereomers which are possible. In case the compounds are racemates that can be split into the optically active in known manner, for example, by means of an optically active acid. However, it is also possible to start with enantiomers or in a given case, even diastereomers, whereby as the final product there is then obtained a correspondingly pure optically active or diastereomeric compound. The (1,2-diphenyl)-ethylenediamine portion, independent of the structure of the group X already has 2 asymmetrical carbon atoms and therefore can be present in the form of the racemate or in left or right rotating form or the meso form. Additional shapes can arise through different enantiomeric or diastereomeric forms of the group X. Especially favorable effects are possessed by the complexes having the same configuration on both centers of asymmetry of the 1,2-diphenyl-ethylenediamine portion.

In regard to the platinum atom, it is a matter of the compounds of the invention of formula I always being the cis-compounds.

The starting amine II is employed for example, as a racemate, meso-compound, as pure right or pure left rotating form or in another diastereomeric form. This configuration is retained in the production of the platinum complex. Especially effective are the racemates of formula I and their optical antipodes.

The process for the production of the compounds I of the invention is carried out in a solvent with a temperature between 10° and 80° C., preferably 15° to 50° C., especially 18° to 25° C. As solvents there can be used for example, water, $C_1$–$C_6$-alkanols (e.g. methanol, ethanol, tert.-butanol or n-hexanol), tetrahydrofurane, dioxane, dimethylsulfoxide, dimethyl formamide, ethylene glycol dimethyl ether, diethyleneglycol dimethyl ether as well as mixtures of these solvents, especially mixtures with water.

The two reactants (platinum compound and Compound II) are preferably employed in equimolar amounts. The pH of the reaction solution should be between 4–7, preferably is in the range pH 6 to 7. The adjustment of the pH is carried out especially by addition of alkali, preferably aqueous sodium hydroxide or potassium hydroxide or for example even by means of sodium bicarbonate.

As tetrahalo-platinum (II) compounds (acid as well as alkali complex salts), there can be used the correspondingf tetrachloro-, tetrabromo- and tetraiodo compounds. The alkali atoms in the alkali-tetrahaloplatinum (II)-complex salts especially are sodium or potassium. However, there can also be used lithium, rubidium or cesium.

The diamine II is suitably employed in the form of an acid addition salt, for example as the dihydrochloride, dihydrobromide, dihydroiodide or as the salt of another acid. Particularly there can also be used acids whose anions form the group X. Furthermore the diamine can be employed in the form of the acetate or diacetate, whereby in a given case before mixing the reaction components potassium chloride is added (for example 2 moles per 1 mole of compound II). Likewise the diamine II can be added in the form of the carbonate.

Free phenolic hydroxy groups present in compounds of formula I can be acylated by $C_2$–$C_6$ alkanoyl groups or by $C_3$–$C_6$-alkenoyl groups. These alkanoyl and alkenoyl groups can contain halogen atoms or $C_1$–$C_4$-alkanesulfonyloxy groups.

This acylation for example can be carried out by means of $C_2$–$C_6$-alkanoyl-halides, e.g. acetyl chloride or acetyl bromide or or $C_3$–$C_6$-alkenoyl halides, e.g. acryloyl chloride or by means of anhydrides of saturated or unsaturated carboxylic acids, e.g. propionyl anhydride or acrylic anhydride, which in a given case are substituted by halogen atoms or $C_1$–$C_4$-alkanesulfonyl groups at a temperature between 10° and 80° C., especially 20°–30° C. in the presence of conventional acid binding material. There can especially be employed as acid binding materials aliphatic tertiary amines such as for example diisopropylethylamine.

As inert solvent or suspension agent for the acylation there can be used for example: lower aliphatic halohydrocarbons (e.g. chloroform), aprotic solvents such as amides, $C_1$–$C_4$-alkylamides and $C_1$–$C_4$-dialkylamides of aliphatic $C_1$–$C_4$-carboxylic acids (e.g. dimethylformamide, dimethylacetamide) N-methylpyrrolidone, dimethyl sulfoxide, pyridine or mixtures of these materials. However, this acylation can also be carried out in a two phase system, for example water/chloroform, whereby the dihydroxy-1,2-bis-(hydroxyphenyl)-ethylenediamine-platinum (II) complex obtained with the help of an anion exchanger is located in the water phase and the mixture of acid chloride and tertiary amine (e.g. diisopropylethylamine) is located in the chloroform phase. As acid halides there are preferably employed the corresponding chloride, bromide and in a given case the iodide.

The exchange of ligand X with another ligand for example can be carried out by means of silver halide precipitation. For this purpose there can be reacted for example a dihalo-(1,2-diphenyl-ethylene-diamine)-platinum (II) compound of formula (I) wherein X indicates a halogen (chlorine, bromine or iodine) in a solvent or suspension agent at a temperature between 10° and 80° C., preferably 30° to 50° C., especially 35° to 45° C. with the silver salt of a different acid which corresponds to the definition of X. However, hereby there can also be used as the silver salt silver nitrate (for example aqueous silver nitrate solution) and there is obtained an ionic diaquo complex of the formula.

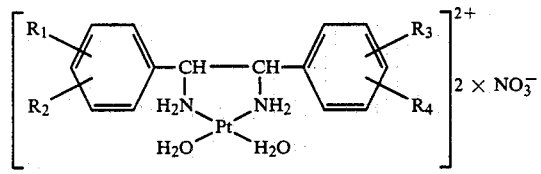

The weakly bound ligand water is easily displaced from this complex by affiner anions (for example $Cl^-$, $Br^-$ in the form of KCl, KBr, malonate$^{2-}$, chloroacetate$^{(-)}$, oxalate$^{2-}$ as well as the remaining stated acid groups X. The acids used here can be employed for example as the free acids or in the form of potassium or sodium salts.

The same compounds can be obtained also by reaction of equimolar amounts of HX and nitrate free platinum complexes (the latter by using anion exchangers in the hydroxide form, for example Dowex 1-8X).

An exchange of the leaving group (for example $SO_4^{2-}$ or oxalate anion$^{2-}$), is also possible in the case of the sulfato or oxalato-(1,2-diphenylethylenediamine)-platinum (II) compounds by reaction with alkaline earth salts, which contain the desired X-ligands (for example glyceric acid), insofar as the complex formed is water soluble and therewith permits the separation of the difficult water soluble alkaline earth sulfate or oxalate.

X-ligands suitable for this process are preferably hydroxycarboxylic acids.

The solvent or suspension agents which were given for the process of production of the compounds I can also be used for the exchange reaction (especially suited are water and dimethylformamide as well as additionally methanol, ethanol, tert.butanol). The exchange reaction is carried out for example in a pH range between 5.5 and 6.

The production of the ($\pm$), (+)– as well as (–) 1,2-bis-(4-methoxy-phenyl)-ethylenediamine from the corresponding meso form is described in J. Med. Chem. Vol. 25 (1982), page 836. The corresponding meso-form is described in Chemische Berichte Vol. 109 (1976), pages 1–40 (32). The production of the free hydroxy compounds is carried out for example by splitting of the ether by means of boron tribromide in methylene chloride at $-20°$ to $-80°$ C., preferably $-60°$ C.

The production of other meso-compounds of formula II can be carried out for example from meso-1,2-bis-(2-hydroxy-phenyl)-ethylenediamine and the corresponding alkoxy substituted benzaldehydes.

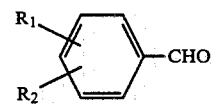

$R_1$ and $R_2$=H or $C_1$–$C_6$-Alkoxy analogous to the process described in Chemische Berichte Vol. 109 (1976) pages 1 et seq. (Diaza-Cope-Rearrangement). This process is especially suited for the production of compounds II in which there are the same type of substituents in both phenyl rings. Conversion of the meso-form into the racemate and separation into the optical isomers can be carried out analogous to J. Med. Chem. Vol. 25 (1982) page 836. The synthesis of the racemate is likewise possible through diazacope rearrangement with d,l-1,2-bis(4-methoxyphenyl)-ethylenediamine or d,l-1,2-bis(2-hydroxyphenyl)-ethylenediamine as starting compounds of the corresponding amine.

Furthermore, starting materials of formula II (especially unsymmetrically substituted) can be obtained in the following manner:

Stilbenes which contain on the two phenyl rings the groups $R_1$, $R_2$, $R_3$ and $R_4$ and can be obtained for example through coupling benzaldehyde which is substituted by the groups $R_1$ and $R_2$ with titanium tetrachloride analogous to the methods described in Chemistry Letters 1973 pages 1041–1044 (published by the Chemial Society of Japan) serve as starting materials. However, this type of stilbene can also be obtained by reaction of benzylmagnesium halides which contain the groups $R_1$ and $R_2$ with unsubstituted or ring substituted benzaldehydes (that is benzaldehyde which contain the groups $R_3$ and $R_4$) analogous to the methods which are described in Berichte der Deutschen Chemischen Gesellschaft Vol 37 (1904) pages 453–458. By addition of N,N-dichlorourethane on the stilbene double bonds there is formed 1-chloro-2-ethoxycarbamoyl-1,2-diphenylethane (with the groups $R_1$, $R_2$, $R_3$ and $R_4$ on the two phenyl rings) which can be base catalyzed cyclized to 2,3-diaryl-aziridines (analogous to the methods described in J. Org. Chemistry Vol. 32 (1967), pages 75–78 and Vol. 31 (1966), pages 3625–3632). Mixed products of cis and trans aziridines are separated by chromatography. From these aziridines there can then be obtained the correspondingly substituted 1,2-diphenylethylenediamines, for example as follows:

The aziridine ring is opened to form 1-azido-2-amino-1,2-diphenylethane by heating (80°–120° C.) with sodium azide in a solvent (lower alcohols, e.g. ethanol, in a given case in admixture with water). In this reaction there arises from the aziridine with aryl rings in the cis position stereospecifically the threo-configured product, or from trans-aziridine the product having the erythro-configuration. The azido group can be reduced to the amine in the customary manner with LiAlH$_4$ in ether.

Splitting of the ether with boron tribromide then leads to hydroxy substituted 1,2-diphenylethylenediamines.

A further possibility for the production of the aziridine is the reaction of the desoxybenzoins containing the groups R$_1$, R$_2$, R$_3$ and R$_4$, accessible through Friedel-Crafts acylation, with hydroxylamine in the customary manner for this type of reaction and reduction of the oxime thus obtained with LiAlH$_4$ in tetrahydrofurane to the aziridine analogous to the procedure described in Tetrahedron Vol. 24 (1968) pages 4605–4623 as well as 6177–6184.

The production of the starting materials II by way of the corresponding stilbenes and aziridines for example can be carried out analogous to the process descriptions given below:

1. Stilbene Synthesis 29 grams (0.2 mole) of 4-chlorobenzaldehyde were dissolved in 300 ml of absolute dioxane and treated at about 10° C. under nitrogen with 33 ml of TiCl$_4$. There were added 39 grams of zinc dust to the golden suspension whereupon the suspension became a black lilac color. The mixture was heated under reflux for 4–5 hours and after cooling off hydrolyzed with 10% K$_2$CO$_3$ solution and extracted with ether. The organic phase was dried over MgSO$_4$, the solvent rotated off and the stilbene recrystallized.

Yield: 75–90%.

2. Aziridine Synthesis 16 grams (0.1 mole) of N,N-dichlorourethane were slowly dropped into the solution of 24.9 grams (0.1 mole) of 4,4'-dichlorostilbene in 50 ml of absolute benzene under nitrogen at 5°–10° C. Subsequently, the mixture was stirred overnight at room temperature. The product was hydrolyzed at 5°–10° C. with 100 ml of 20° NaHSO$_3$ solution, shaken with ether, the organic phases were washed with 20% NaCl solution, dried and the solvent rotated off. The product remained as an oily residue which was recrystallized from ethanol.

Yield: 68% [1-chloro-2-ethoxycarbamoyl-1,2-bis-(4-chlorophenyl)-ethane].

0.1 mole of the β-chlorocarbamate thus obtained, dissolved in 100 ml of 96% ethanol; were added to a solution of 30 grams (0.5 mol) of KOH in 235 ml of 96% ethanol. The reaction mixture was stirred for 4 hours at 50° C. The mixture was diluted with double the volume of water, extracted with ether or methylene chloride, the organic phase dried and the solvent driven off. The product mixture of cis- and trans-aziridine was separated by chromatography on silica gel using benzene/methylene chloride as eluation agent.

Yield: 45% [2,3-bis-(4-chlorophenyl)-aziridine].

3. Ring Opening With Azide 20 mmole of aziridine were dissolved in 80 ml of ethanol and treated with 5.2 grams (80 mmoles) of NaN$_3$ and 4.3 grams (80 mmole) of NH$_4$Cl in 27 ml of water and heated for 14–18 hours under reflux. Subsequently, the product was diluted with water and shaken with ether or methylene chloride. After the drying and rotating off of the solvent there remained the product as a crystalline residue which was recrystallized from petroleum ether.

Yield: 74% [1-azido-2-amino-1,2-bis-(4-chlorophenyl)ethane].

Starting materials of formula II wherein one or more of the groups R$_1$, R$_2$, R$_3$ and R$_4$ represents a hydroxy group can be acylated on the hydroxy groups by a C$_2$–C$_6$-alkanoyl group or C$_3$–C$_6$ alkenoyl group which alkanoyl or alkenoyl group as stated above in a given case is substituted. This acylation can be carried out in inert solvents or suspension media such as dioxane, dimethylformamide benzene or toluene at a temperature between 0° to 200° C., preferably 20° to 150° C. As acylating agent there can be used for example: acyl halides (chloride, bromide, iodide) or acid anhydride of the corresponding carboxylic acids having 2 to 6 carbon atoms (which as stated in a given case can be substituted). This acylation in a given case can be carried out with addition of an acid binding agent such as alkali carbonates, e.g. sodium carbonate and potassium carbonate, alkali hydroxides, e.g. sodium hydroxide and potassium hydroxide, alkaline alcoholates, e.g. sodium ethylate, or a tertiary amine, for example triethylamine or diisopropylethylamine.

Another possibility is the acylation of the diamine resulting from the diimine resulting from the diazacope-rearrangement, for example protected 1,2-bis-(4-hydroxyphenyl)-ethylenediamine (both amino groups being protected by the 4-methoxybenzylidene group) obtained from N,N'-bis-(4-methoxybenzylidene)-1,2-bis(4-methoxyphenyl)ethylenediamine by splitting of the ether with BBr$_3$. The acylation of the 1,2-bis(hydroxyphenyl)ethylenediamine with benzal protective groups can be carried out in the manner previously described. As acid binding agent there can also be used pyridine, whereby pyridine simultaneously also can serve as solvent.

The benzaldehyde derivative serving as protective group is subsequently separated off through hydrolysis and steam distillation.

The compounds of the invention are suited for the production of pharmaceutical compositions. The pharmaceutical compositions or medicaments can contain one or more of the compounds of the invention or mixtures of the same with other pharmaceutically effective materials. For the production of pharmaceutical preparations there can be used the customary pharmaceutical carriers, diluents and excipients. The medicines for example can be used internally, parenterally (for example intraveneously, intramuscularly, subcutaneously) or orally. For example dispensation can be carried out in the form of tablets, capsules, pills, dragees or plugs. As liquids there can be used for example oily or aqueous solutions or suspensions (for example in sesame oil or olive oil), emulsions, injectable aqueous and oily solutions or suspensions. Furthermore there can be produced for example dry ampoules which contain compound I of the invention as active material, whereby before use the contents of such dry ampoules are dissolved for example in physiological salt solution or mixtures of physiological salt solution and for example dimethyl sulfoxide.

Examples of excipients and additives of this kind are the substances recommended and specified in the following literature references as additives for pharmacy, cosmetics and related fields: Ullmanns Encyklopaedie der technischen Chemie, Vol. 4 (1953), pages 1 to 39; Journal of Pharmaceutical Sciences, Vol. 52 (1963), pages 918 et seq., H.v.Czetsch-Lindenwald, Hilfsstoffe fur Pharmazie und angrenzende Gebiete; Pharm. Ind., No. 2, 1961, pages 72 et seq.; Dr. H. P. Fiedler, Lexikon der Hilfsstoffe fur Pharmazie Kosmehk und angrenzende Gebiete Cantor KG. Aulendorf (Wurtt.) 1971.

Examples of such materials include gelatin, natural sugars such as sucrose or lactose, lecithin, pectin, starch (for example cornstarch), alginic acid, tylose, talc, lycopodium, silica (for example colloidal silica), glucose, cellulose, cellulose derivatives, for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methyl stearate and glyceryl stearate, magnesium and calcium salts of fatty acids with 12 to 22 carbon atoms, especially saturated acids (for example, calcium, stearate, calcium laurate, magnesium oleate, calcium palmitate, calcium behenate and magensium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono-, di-, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate,, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamine, lactamide, lactates, e.g., ethyl lactate, ethyl carbonate, silicones (especially medium viscosity dimethyl polysiloxane), magnesium carbonate and the like.

As further adjuvants there can also be used materials which cause decomposition (so-called disintegrants) such as cross-linked polyvinyl pyrrolidone, sodium carboxymethyl starch, sodium carboxymethyl cellulose or microcrystalline cellulose. Likewise there can be used known encasing agents such as for example: polyacrylate acid esters, cellulose ethers and the like.

For the production of solutions, there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., glyceryl monostearate, glyceryl distearate, glyceryl monopalmitate, paraffins, and the like.

In the production of the composition, there can be used known and customary solutions aids or emsulifiers. As solution aids and emulsifiers, there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyoleotriglycerides, linolized oleotriglycerides, polyethylene oxide-condensation products of fatty alcohols, alkylphenols or fatty acids or also 1-methyl-3-(2-hydroxyethyl)-imidazolidone-2. As used herein, polyoxyethylated means that the materials in questions contain polyoxyethylene chains whose degree of polymerization generally is between 2 and 40, particularly between 10 and 20.

Such polyoxyethylated materials, for example, can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191–195).

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffes. Generally, there is preferred a neutral to weak acid (to pH 5) pH value.

As antioxidants, there can be used, for example, sodium meta bisulfite, ascorbic acid, gallic acid, alkyl gallates, e.g., methyl gallate and ethyl gallate, butyl hydroxyanisole, nordihydroguajarehc acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmacological and galenical treatment of the compounds of the invention is carried out according to the usual standard methods. For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides, reference is made to the following standard textbook: Sucker, Fuchs, Speiser, Pharmazeutische Technologie, Thieme-Verlag, Stuttgart, 1978.

The active principles or medicaments may be applied to the skin or mucosa or into the interior of the body, for example orally, enterally, pulmonarily, rectally, nasally, vaginally, lingually, intraveneously, intraarterially, intracardially, intramuscularly, intraperitoneally, intracutaneously or subcutaneously.

In the form of parenteral preparation it is a matter particularly of sterile or sterilized products.

The compounds of the invention in vivo show a good antitumor activity on ADJ/PC 6 plasmacyloma and on leukemia L 5222 as well as in vitro on the MDA-MB 231 and MCF-7 mammary tumor cell line. For example on ADJ/PC 6 Plasmacytom of the Balb/C-mouse at a dosage of $3 \times 20$ mg/kg mouse there is atained a % T/C value of "zero", i.e. none of the animals is able to develop a tumor. In the rat leukemia L 5222 in a dosage of $3 \times 20$ mg/kg there is attained an increase of the survival time up to 175% ILS. On the MDA-MB 231 cell line in a concentration of $1 \times 10^{-5}$ mole/l there is produced a 90% inhibition of the incorporation of $[^3H]$-thymidine, on the MCF-7 cell line at the same concentration a 95% inhibition.

This antitumor action is comparable with the action of the known medicine cisplatin or is better than cisplatin. The lowest antitumorally effective dosage in the above stated animal experiments for example is $3 \times 10$ mg/kg ip (ADJ/PC6) and about $3 \times 15$ mg/kg ip L 5222. Dosage range for the action for example there is used $3 \times 20$ mg–$3 \times 30$ mg/kg ip. (ip—intraperitoneally).

Indications for which the compounds of the invention may be used include bronchial, testes, ovarial, cervix, prostate, endometrium, bladder carcinoma, melanoma, carcinoma in the throat-head-region.

Contraindications

Pregnancy, heavy depressions of the bone marrow

The new compounds of the invention possess a marked tumor retarding action with good compatibility. The tumor retarding action is shown particularly in the following animal and cell culture models: leukemia (for example Leukemia L 5222 of the rat and L 1210 of the mouse); plasma cell tumors (for example ADJ/PC 6 plasmacytoma of the mouse); hormone dependent tumors (B16 melanoma of the mouse, human MCF7 mammary carcinoma cell line); cytostatica-resistant tumors (cisplatin and Daunomycin-resistant Ehrhich ascites tumor of the mouse). Furthermore they also possess a cytostatic action on hormone-independent mammary carcinoma cells (MDA-MB 231).

The pharmaceutical preparations generally contain from 100 to 200 mg, preferably 150 mg of the active component(s) according to the present invention.

The preparations may be administered, for example in the form of tablets, capsules, pills, dragees, suppositories, ointments, jellies, creams, powders, dusting powders, aerosols or in liquid form. Examples of liquid formulations are oily or alcoholic or aqueous solutions, suspensions and emulsions. Preferred formulations are tablets containing from 100 to 200 mg of active substance, or solutions containing from 0.02 to 0.040% of active substance.

The active components according to the present invention may be used in individual doses of, for example;
(a) from 100 to 200 mg, preferably 150 mg in the case of oral formulations,
(b) from 100 to 200 mg/m², preferably 150 mg/m² in the case of parenteral formulations (as intravenous permanent infusion),
(c) from 1 to 5%, preferably 2.5% in the case of local applications to the skin and mucous membrances (for example in the form of solutions, lotions, emulsions, salves, etc.).

For example, 1 to 4 tablets containing from 100 to 200 mg of active substance may be prescribed three times daily or, for example, in the case of intravenous injection of a permament infusion of 1000 ml content containing 100 to 200 mg active substance/m² body surface. In the case of oral administration, the minimum daily dose is, for example 300 mg, while the maximum daily dose should not exceed 800 mg.

The acute toxicity of the compounds according to the present invention in mice (expressed by the LD 50 mg/kg; method according to Miller and Tainter; Proc. Soc. Exper. Biol. a. Med. Vol. 57 (1944) 261) is above 120 mg/kg in the case of, for example ip application.

The medicaments may be used in human medicine.

Unless otherwise indicated, all parts and percentages are by weight.

The compositions can comprise, consist essential of, or consist of the materials set forth.

The methods can comprises, consist essentially of, or consist of the steps set forth with the materials shown.

EXAMPLE 1

(+)-Dichloro-[1,2-bis(4-hydroxy-phenyl)-ethylenediamine]-platinum (II).

There were dropped into a solution of 830 mg (2 mmole) of $K_2PtCl_4$ in 6 ml of water, 2 mmole of (+)-1,2-bis-(4-hydroxy-phenyl)-ethylenediaminedihydrobromide dissolved in 4 ml of water. The solution was neutralized with 0.5N NaOH, whereby a yellow precipitate formed. The mixture was stirred at room temperature with the exclusion of light and neutralized at intervals of 1–2 hours. After 9–10 hours it was filtered with suction, washed free of chloride with water and dried. The mother liquor was stirred further and neutralized several times. After about 4 days the constance of the pH indicated the end of the reaction. It was filtered with suction several times and the precipitate handled in the manner stated above. The thus obtained yellow powder is very dielectric (Yield: 94%).

Purification:

1020 mg (2 mmole) of the precipitated complex were finely ground in a mortar, made into a suspension in 150 ml of $H_2O$ and stirred with 697 mg (4.1 mmole) of silver nitrate (dissolved in 40 ml of water) for 15 hours at room temperature, whereby the corresponding nitrato complex is formed. The silver halide formed was centrifuged out. Excess silver ions were precipitated out of the supernatant solution with 0.5N hydrochloric acid and the mixture centrifuged again. The solution of the nitrato complex was separated off, treated with 8 mmole of potassium chloride (dissolved in 5 ml of water), neutralized and stirred for several hours. The purified complex was filtered off with suction, washed and dried. M.P.: 340°–350° C. (with decomposition).

Yield: 50%

IR spectrum in KBr: 3260 s, 3195 s (NH), 1620 s, 1600 s, 1520 s (NH), 1250 s, 1180 s, 830 s, 810 m, 770 m, 565 m, 530 m (PtN), 320 m (PtCl)

(−)- and (±)-Dichloro-[1,2-bis-(4-hydroxy-phenyl)-ethylenediamine]-platinum (II) were produced analogously.

(±)-Dichloro-[1,2-bis(4-hydroxy-phenyl)-ethylenediamine]-platinum (II)

M.P.: 355°–358° C. (with decomposition)

Yield: 88%, yellow powder

IR-Spectrum in KBr: 3260 s, 3195 (NH), 1620 s, 1520 s, (NH) 1450 m, 1260 s, 1240 m, 1180 s, 830 s, 810 s, 765 m, 610 m, 570 m (PtN), 320 m (PtCl)

(−)-Dichloro-[1,2-bis-(4-hydroxy-phenyl)-ethylenediamine]-platinum (II)

M.P.: 340°–350° C. (with decomposition)

IR-Spectrum: see (+)-Dichloro-[1,2-bis-(4-hydroxy-phenyl)-ethylenediamine]-platinum (II).

s=sharp bond, m=medium bond

Production of the Starting Material II

The production of the corresponding (±), (+)- and (−) methyl ether is given in J. Med. Chem. Vol. 25 (1982), page 836. The free hydroxy compounds can be produced therefrom for example by splitting the ether according to the following procedure:

3.54 grams (13 mmole) of (−)-1,2-bis(p-methoxy-phenyl)ethylenediamine were dissolved in 130 ml of absolute methylene chloride and cooled to −60° C. At this temperature there were added 4.95 ml (53 mmole) of boron tribromide and stirring was carried out for 30 minutes in a cooling bath. Subsequently the mixture was allowed to warm to room temperature and stirring continued overnight. Using an ice-sodium chloride solution it was hydrolyzed with 10 ml of methanol and rotated until dry. For the purpose of purifiation the product was taken up in methanol and precipitated with ether.

Yield: 3.3 grams (63%).

IR: 3100 s very broad, 2000 w broad (NH), 1640 s, 1605 s, 1545 s, 1520 s, 1505 s, 1290 s, 1260 s, 1215 s, 860 s, 770 m.

EXAMPLE 2

(−)-Sulfato-[1,2-bis-(4-hydroxy-phenyl)-ethylenediamine]-platinum (II)×2H$_2$O.

1020 mg (2 mmole) of (−)-dichloro-[1,2-bis-(4-hydroxy-phenyl)-ethylenediamine]-platinum (II) were finely ground and suspended in 100 ml of water. The suspension was heated to 40° C. and treated with 624 mg (2 mmole) of Ag$_2$SO$_4$ (dissolved in 80 ml of water) and stirred overnight with the exclusion of light. Subsequently, the mixture was filtered, a small sample tested in the cold for silver ions with 0.1N HCl and the solution concentrated to 5 ml on the rotary evaporator. The precipitate was filtered off with suction, washed with ice water and dried. White Powder: M.P. about 295° C. (at 250° there was coloration).

The compound contains 2 molecule parts of water.

Yield: 30%

IR-Spectrum in KBr: 3200 s broad, 1610 m, 1520 s, 1250 s, 1180 s, 1120 s, 1020 s, 830 m.

EXAMPLE 3

(−)-1,1-Cyclobutanedicarboxylate-[1,2-bis-(4-hydroxy-phenyl)-ethylenediamine]-platinum (II) 1020 mg (2 mmole) of (−)-dichloro-[1,2-bis-(4-hydroxy-phenyl)-ethylenediamine]-platinum (II) were ground fine and suspended in 150 ml of water. The suspension heated to 60° C. was treated with 645 mg (3.8 mmole) of AgNO$_3$ (dissolved in 5 ml of water) and stirred overnight at room temperature with the exclusion of light. After concentration in the rotary evaporator to 30 ml the mixture was filtered and the filtrate treated with a solution of 274 mg (1.9 mmole) of 1,1-cyclobutanedicarboxylic acid in 25 ml of water and subsequently slowly brought to a pH of 5.5–6.0 with 0.1N NaOH. Then the mixture was concentrated to about 15 ml (in the rotary evaporator), filtered with suction, washed and dried over P$_2$O$_5$.

White powder. M.P. about 303° C. (coloration beginning at 280°).

The compound contains 1 molecule of water

Yield: 24%

IR-Spectrum in KBr: 3100 s broad, 1630 s, 1640 s, 1400 s, 850 s.

EXAMPLE 4

Meso-Dichloro-[1,2-bis-(3,4-dimethoxy-phenyl)-ethylene-diamin]-platinum (II) 332 mg (1 mmole) of 1,2-bis-(3,4-dimethoxy-phenyl)-ethylene-diamine were dissolved in 150 ml of hot 0.02N HCl. The solution was slowly added with stirring to a solution of 415 mg of K$_2$PtCl$_4$ in 5 ml of H$_2$O. The solution was neutralized with 0.5N NaOH and treated with about 2 grams of KCl. The mixture was stirred at about 70° with the exclusion of light and neutralized at intervals of 1–2 hours. After 12 hours the mixture was filtered with suction, washed with 0.5N HCl H$_2$O and acetone and dried.

M.P. about 280° (decomposition)

Yield: 79%, yellow powder.

IR-Spectrum in KBr: 3220 s, 3110 m (NH), 2920 m (CH), 1595 m, 1520 s, 1270 s, 1030 s, 805 m, 765 m, 535 w, 330 m (PtCl)

EXAMPLE 5

Meso-Dichloro-[1,2-bis-(4-methoxy-phenyl)-ethylenediamine]-platinum (II) 415 mg (1 mmole) of K$_2$PtCl$_4$ dissolved in about 10 ml of 40% warm t-butanol were treated with 272 mg (1 mmole) of 1,2-bis(p-methoxy-phenyl)-ethylenediamine in 40 ml of 50% t-butanol. Stirring was carried out for 2 hours at 50° C. with the exclusion of light. The product was filtered off with suction, washed with water and t-butanol and dried.

M.P. about 220° C. (decomposition).

Yield: 84%, light yellow powder.

IR-Spectrum in KBr: 3240 m (NH), 1610 s, 1580 s, 1510 s (NH), 1460 m, 1250 s, 1180 s, 1030 s, 540 m, 315 m (PtCl).

The following compounds were produced in a manner analogous to Example 1

EXAMPLE 6

(±)-Dichloro-[1,2-bis-(3-methoxy-phenyl)-ethylenediamine]-platinum (II)

M.P.: about 335° C. (decomposition)

Yield: 83%, yellow powder

IR-Spectrum in KBr: 3270 s (NH), 2950 m (CH), 1600 s, 1300 s, 1235 s, 790 s, 700 s, 560 w, 465 w, 325 m (PtCl)

EXAMPLE 7

(±)-Dichloro-[1,2-bis-(3-hydroxy-phenyl)-ethylenediamine]-platinum (II)

M.P.: about 360° C. (decomposition)

Yield: 68%, yellow powder

IR-Spectrum in KBr: 3260 s, 3200 m (NH), 1600 s, 1465 s, 1220 s, 705 s, 470 m, 320 m (PtCl)

EXAMPLE 8

Meso-Dichloro-[1,2-bis-(3-hydroxy-phenyl)-ethylenediamine]-platinum (II)

M.P.: about 275° C. (decomposition)

Yield: 53%, light yellow powder
IR-Spectrum in KBr: 3200 s, 3110 m (NH), 1590 s, 1460 s, 1045 m, 780 s, 705 s, 535 w, 325 m (PtCl)

EXAMPLE 9

(±)-Dichloro-[1,2-bis(4-methoxy-phenyl)-ethylenediamine]-platinum (II)

M.P.: about 335° C. (decomposition)
Yield: 55%, yellow powder
IR-Spectrum in KBr: 3260 s, 2310 m, 3170 s (NH), 1610 s, 1580 m, 155 m (NH), 1460 s, 1250 s, 1180 s, 1040 s, 825 s, 530 m, 310 (PtCl)

EXAMPLE 10

Threo-Dichloro-[1-(4-hydroxy-phenyl)-2-phenyl-ethylenediamine]-platinum (II)

M.P.: about 280° C. (decomposition)
Yield: 57%, light yellow powder
IR-Spectrum in KBr: 3200 s, 3100 m (NH), 1610 m, 1570 m, 1500 s, 1175 s, 755 m, 700 m, 520 w, 325 m (PtCl)

EXAMPLE 11

Threo-Dichloro [1-(4-methoxy-phenyl)-2-phenyl-ethylenediamine]-platinum (II)

M.P.: about 280° C. (decomposition)
Yield: 57%, light yellow powder
IR-Spectrum in KBr: 3200 s, 3100 s (NH), 1610 m, 1570 m, 1510 s, 1260 s, 1070 s, 710 s, 320 m (PtCl)

EXAMPLE 12

Dichloro-[1-(3,4-dimethoxy-phenyl)-2-phenyl-ethylenediamine]-platinum (II)

M.P.: about 335° C. (decomposition)
Yields: 85%, yellow powder
IR-Spectrum in KBr: 3240 s (NH), 1600 m, 1520 s, 1320 s, 1150 s, 1030 s, 770 m, 710 m,. 520 w, 320 m (PtCl)

PRODUCTION OF THE STARTING MATERIALS FOR EXAMPLES 4–12

The starting materials of formula II were employed as the hydrobromide or hydrochloride. The hydrobromides of the hydroxy compounds were isolated after the splitting of the ether with boron tribromide. To produce the hydrochloride the base of the corresponding compound was dissolved in alcohol, HCl led in and the product precipitated with ether.

The hydrochloride can be produced from the hydrobromide by reaction with an ion exchanger, separation of the aqueous solution and evaporation of the water.

COMMON PROCEDURE FOR THE SYNTHESIS OF STARTING MATERIALS II

The starting compounds for Examples 4–9 were produced according to the process which is described in Chemische Berichte, Vol. 109 (1976), pages 1 et seq. The splitting of the ether is carried out with boron tribromide as is stated under Example 1 (in production of starting material II). 1-(4-methoxy-phenyl)-2-phenyl-ethylenediamine (starting material for Example 11) was produced from trans-4-methoxy-stilbene in a manner analogous to the process set forth above (see under stilbene synthesis aziridine synthesis).

Meso-1,2-Bis(3-methoxyphenyl)ethylenediamine (M.P. 115°–117° C.)

This compound was produced analogous to the method given in J. Med. Chem. Vol. 75 (1982), pages 836 et seq. for the production of 1,2-bis-(4-methoxy-phenyl)-ethylenediamine.

Meso-N,N'-bis(3-methoxybenzylidene)-1,2-bis(3-methoxyphenyl)-ethylenediamine (M.P. 120° C. from acetonitrile). Synthesis analogous to J. Med. Chem. Vol. 25 (1982), pages 836 et seq.

(±)-1,2-Bis(3-methoxyphenyl)ethylenediamine

The previously mentioned diimine was melted and stirred at 150°–160° C. for about 15 minutes. After cooling to about 90° C. it was treated with 3N $H_2SO_4$ and subjected to a steam distillation. The solution remaining behind was filtered hot, brought to pH 2 at 0°–20° C. and treated with ethanol. The sulfate crystallized out was separated off, the base set free with NaOH, shaken with methylene chloride/chloroform and rotated. The product remained as an oily residue.

IR-Spectrum (Film): 3400 broad, 1600 s, 1500 s, 1270 s, 1050 m, 710 s meso- and (±)-1,2-Bis(3,4-dimethoxyphenyl)ethylenediamine.

These compounds can be produced analogous to the 4-mono-substituted diamines according to J. Med. Chem. Vol. 25 (1982), page 836 et seq.

M.P. of the meso-form 185.5°–187° C. (from chloroform)
M.P. of the (±)-form 82°–83° C.

Threo- and erythro-1-(4-methoxyphenyl)-2-phenylethylenediamine

This compound was obtained from 4-methoxystilbene according to the process described above and subsequent reduction of the azide with $LiAlH_4$ in absolute diethyl ether. 15.2 mmoles of azide in 60 ml of absolute ether were dropped into the suspension of 1.4 grams of $LiAlH_4$ in 70 ml of absolute ether with ice cooling, subsequent heating of the mixture, under reflux (4.5 hours), cooling and hydrolysis with water.

4-Methoxystilbene (M.P. 130°–131° C.)

19.6 grams (0.1 mole) of 4-hydroxystilbene, 135 grams of $K_2CO_3$ and 135 grams of methyl iodide were stirred in 500 ml of dimethyl-formamide for 20 hours at room temperature. After dilution with water the mixture was shaken with methylene chloride.

Threo-1-(4-methoxyphenyl)-2-phenylethylenediamine (oil; IR-Spectrum (Film): 3390 m, 3310 m ($NH_2$), 1610 s, 1510 s, 1270 s, 1070 s, 1040 s); erythro-1(4-methoxyphenyl)-2-phenylethylenediamine (M.P. 90°–91° C.) and 1-(3,4-Dimethoxyphenyl)-2-phenylethylenediamine (oil; IR-Spectrum (Film): 3380 m, 3310 m ($NH_2$), 2950 (CH aliphatic, 1600 m, 1510 s, 1470 s, 1260 s, 1140 s, 1030 s) were produced from the corresponding aziridines with opening of the ring with azide and subsequent reduction with $LiAlH_4$ (see the production of the starting material). For example 1-(3,4-dimethoxyphenyl)-2-phenylethylene-diamine was obtained via 1-oximino-1-(3,4-dimethoxy-phenyl)-2-phenyl-ethane. The reduction of the oxime with $LiAlH_4$ was carried out as follows:

To the suspension of 760 mg (20 mmole) of $LiAlH_4$ in 16 ml of absolute tetrahydrofurane there were slowly dropped in 2.71 grams (10 mmole) of oxime dissolved in 70 ml of absolute tetrahydrofurane. Subsequently the mixture was heated for 3 hours under reflux. It was hydrolyzed with H₂O with ice cooling, filtered with suction from aluminum hydroxide and extracted with ether. After removal of the solvent the aziridine remained as a yellow oil.

The free hydroxy compounds were produced from the methyl ethers by splitting of the ether according to the method described above. (±)-1,2-Bis(3-hydroxyphenyl)ethylenediamine IR-Spectrum (KBr): 3340 m, 3290 m (NH), 1610 s, 1460 s, 1160 m meso-1,2-Bis(3-hydroxyphenyl)ethylenediamine IR-Spectrum (KBr): 3370 m, 3340 m (NH), 1600 s, 1470 s, 1260 s threo-1-(4-hydroxy-phenyl)2-phenylethylenediamine dihydrobromide IR-Spectrum (KBr): 3400 m, 3000 s broad (NH, OH), 1600 s, 1530 s, 720 s Erythro-1-(4-hydroxyphenyl)2-phenylethylenediamine dihydrobromide IR-Spectrum (KBr): 3400 m, 3000 s broad (NH, OH), 1590 s, 1510 s, 1290 s, 1060 s.

Example For Injection Solution 9 grams of sodium chloride were dissolved with stirring in 800 ml of water suitable for injection purposes and the pH adjusted to 2.5–3.5 (preferably 3.0) with the help of concentrated hydrochloric acid (38%). Then with stirring there was dissolved 1 gram of the material (+)-dichloro[1,2-bis-(4-hydroxy-phenyl)-ethylenediamine]-platinum II. The pH is controlled and, in case it is necessary again adjusted to 2.5–3.5 with hydrochloric acid. Finally the volume was filled up to 1 liter with water suitable for injection purposes and the pH was again checked.

This solution was sterile filtered under aseptic conditions via a membrane filter having a pore diameter of 0.22 μm and filled to 50 ml in 50 ml injection flasks (brown) of hydrolytic class I. The injection flasks were closed with Teflon coated rubber stoppers and provided with aluminum flanged lids. 1 ml of solution contains 1 mg of active material.

Example For Lyophilizate

There were dissolved with stirring 9 grams of sodium chloride and 10 grams of mannitol in 800 ml of water suitable for injection purposes. The pH was adjusted with concentrated hydrochloric acid (38%) to a pH of 2.5–3.5 (preferably 3.0). There was dissolved in this solution with stirring 1 gram of the material (+)-dichloro [1,2-bis-(4-hydroxyphenyl)-ethylenediamine]-platinum (II). The pH was controlled and in case it is necessarily adjusted again with hydrochloric acid to 2.5–3.5. Finally the volume was filled to 1 liter with water suitable for injection purposes and the pH checked again.

This solution was sterile filtered under aseptic conditions via a membrane filter having a pore diameter of 0.22 μm and filtered to 10 ml in brown 15 ml injection flasks of hydrolytic class I. These flasks were provided with a freeze drying stopper and lyophilized in a suitable plant. After drying the flasks were gassed with sterile, dry nitrogen and the flasks finally closed in the plant. The stoppers were secured by a border lid.

For intravenous use the lyophilizate is reconstituted in 10 ml of water suitable for injection purposes.

1 ml of solution contains 1 mg of active material.

The entire disclosure of German priority application No. P 3305636.6 is hereby incorporated by reference.

What is claimed is:

1. A (1,2-diphenyl-ethylenediamine)-platinum (II) complex compound of the formula

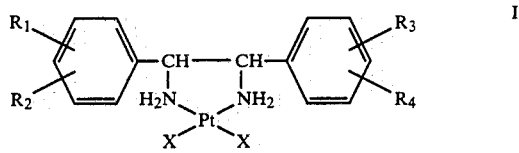

where the groups $R_1$, $R_2$, $R_3$ and $R_4$ are hydrogen, hydroxy, $C_1$–$C_6$-alkoxy, $C_2$–$C_6$-alkanoyloxy, $C_2$-alkanoyloxy substituted by at least one halogen atom or a $C_1$–$C_4$-alkanesulfonyloxy group, or $C_3$–$C_6$-alkenoyloxy, with the proviso that at least one of $R_1$, $R_2$, $R_3$ and $R_4$ is not hydrogen and X is the equivalent of a pharmaceutically compatible anion.

2. A compound according to claim 1 wherein $R_1$ is hydroxy or methoxy, $R_2$ is hydroxy, methoxy or hydrogen, $R_3$ is hydroxy, methoxy or hydrogen and $R_4$ is hydroxy, methoxy or hydrogen.

3. A compound according to claim 2 wherein $R_1$ is hydroxy, $R_2$ is hydrogen, $R_3$ is hydroxy and $R_4$ is hydrogen.

4. A compound according to claim 2 wherein $R_1$, $R_2$, $R_3$ and $R_4$ are all methoxy.

5. A compound according to claim 2 wherein $R_1$ is methoxy, $R_2$ is hydrogen, $R_3$ is methoxy and $R_4$ is hydrogen.

6. A compound according to claim 2 wherein $R_1$ is hydroxy and $R_2$, $R_3$ and $R_4$ are all hydrogen.

7. A compound according to claim 2 wherein $R_1$ is methoxy and $R_2$, $R_3$ and $R_4$ are all hydrogen.

8. A compound according to claim 2 wherein $R_1$ is methoxy, $R_3$ is hydrogen and $R_4$ is hydrogen.

9. A pharmaceutical composition comprising a compound according to claim 1 in an amount effective to retard the growth of a tumor and a pharmaceutically acceptable carrier.

10. A compound according to claim 1 wherein X is chloro, sulfato, or cyclobutanedicarboxylic acid.

11. A compound according to claim 2 wherein X is chloro, sulfato, or cyclobutanedicarboxylic acid.

12. A compound according to claim 1 wherein X is the anion of one of the following acids, hydrochloric acid, nitric acid, hydrobromic acid, hydriodic acid, sulfuric acid, phosphoric acid, camphor sulfonic acid, an aliphatic sulfonic acid, an aromatic sulfonic acid, an aliphatic $C_2$–$C_4$ monocarboxylic acid, a halogen substituted aliphatic $C_2$–$C_4$ monocarboxylic acid, an aliphatic $C_2$–$C_{11}$ dicarboxylic acid, an aliphatic $C_2$–$C_{11}$ dicarboxylic acid substituted in the 2-position by a $C_1$–$C_4$-alkyl group, an aliphatic monohydroxy monocarboxylic acid having 2 to 6 carbon atoms, an aliphatic dihydroxy monocarboxylic acid having 2 to 6 carbon atoms, an aliphatic monohydroxy di or tricarboxylic acid having 3 to 8 carbon atoms, an aliphatic dihydroxy di or tricarboxylic acid having 3 to 8 carbon atoms, phthalic acid, phthalic acid substituted by a carboxyl group, isophthalic acid, terephthalic acid, gluconic acid, glucuronic acid, cyclobutanedicarboxylic acid, an aldose phosphoric acid, a ketose phosphoric acid, glycerine phosphoric acid, N-phosphonoacetyl aspartic acid.

13. A pharmaceutical composition comprising a compound according to claim 1 in an amount of 100 to 200 mg and a pharmaceutically acceptable carrier.

14. A compound according to claim 1 which is the nitrato complex of [1,2-bis(4-hydroxy-phenyl)-ethylenediamine-platinum (II).

* * * * *